(12) United States Patent
Cestero et al.

(10) Patent No.: US 11,596,394 B2
(45) Date of Patent: Mar. 7, 2023

(54) ADJUSTABLE LOCKING SURGICAL RETRACTOR

(71) Applicant: Board of Regents, the University of Texas System, Austin, TX (US)

(72) Inventors: Ramon Francisco Cestero, San Antonio, TX (US); Justin Alexander Long, San Antonio, TX (US); Clarence Lamar Long, San Antonio, TX (US); Jeffrey Adam Long, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/276,816

(22) PCT Filed: Sep. 17, 2019

(86) PCT No.: PCT/US2019/051549
§ 371 (c)(1),
(2) Date: Mar. 16, 2021

(87) PCT Pub. No.: WO2020/061073
PCT Pub. Date: Mar. 26, 2020

(65) Prior Publication Data
US 2021/0346006 A1 Nov. 11, 2021

Related U.S. Application Data

(60) Provisional application No. 62/732,340, filed on Sep. 17, 2018.

(51) Int. Cl.
*A61B 17/02* (2006.01)
(52) U.S. Cl.
CPC ...... *A61B 17/0293* (2013.01); *A61B 17/0206* (2013.01)

(58) Field of Classification Search
CPC .. A61B 17/02; A61B 17/0206; A61B 17/0293
See application file for complete search history.

(56) References Cited

U.S. PATENT DOCUMENTS

| | | | |
|---|---|---|---|
| 1,706,500 A * | 3/1929 | Smith | A61B 17/02 600/245 |
| 1,919,120 A | 7/1933 | O'Connor et al. | |

(Continued)

FOREIGN PATENT DOCUMENTS

| | | |
|---|---|---|
| CN | 203001015 U | 6/2013 |
| EP | 1195141 | 4/2002 |

(Continued)

OTHER PUBLICATIONS

PCT international preliminary report on patentability, PCT/US2019/051549, dated Mar. 25, 2021, The International Bureau of WIPO, Switzerland.

*Primary Examiner* — Julianna N Harvey (57) ABSTRACT

A surgical retractor assembly for providing surgical exposure. The surgical retractor assembly consists of two frame segments connected by adjustable ratchet mechanisms to form a retractor frame. The ratchet mechanisms can be attached to tissue retractor blades that provide exposure of the wound when expanded, without the requirement of a direct connection/attachment to an operating table or bed frame. The tissue retractor blades are attached in a manner that is adjustable and facilitates the ability of the overall surgical retractor assembly to be raised or lowered with respect to the patient. The retractor frame also allows attachments of additional retractor blades or other surgical retractor accessories for additional surgical exposure.

18 Claims, 9 Drawing Sheets

(56) References Cited

U.S. PATENT DOCUMENTS

| | | | |
|---|---|---|---|
| 1,963,173 A * | 6/1934 | Morin | A61B 17/0293 600/233 |
| 2,013,892 A * | 9/1935 | Lucas | A61B 17/0293 600/234 |
| 2,053,868 A * | 9/1936 | Grosso | A61B 17/0293 600/233 |
| 5,231,974 A * | 8/1993 | Giglio | A61B 17/0293 600/233 |
| 6,468,207 B1 | 10/2002 | Fowler, Jr. | |
| 6,808,493 B1 * | 10/2004 | Bookwalter | A61B 17/02 600/233 |
| 8,900,137 B1 | 12/2014 | Lovell et al. | |
| 9,216,016 B2 | 12/2015 | Fiechter et al. | |
| 11,228,235 B2 * | 1/2022 | Cestero | A61B 17/0293 |
| 2002/0183833 A1 | 12/2002 | Stevens et al. | |
| 2003/0065251 A1 | 4/2003 | Feng et al. | |
| 2004/0092797 A1 * | 5/2004 | Yi | A61B 17/0281 600/210 |
| 2004/0230191 A1 * | 11/2004 | Frey | A61B 17/7082 606/57 |
| 2009/0287062 A1 | 11/2009 | Farley et al. | |
| 2010/0280586 A1 | 11/2010 | Case et al. | |
| 2012/0296170 A1 * | 11/2012 | Wilkins | A61B 17/0293 600/206 |
| 2014/0114137 A1 | 4/2014 | Reglos et al. | |
| 2018/0234009 A1 | 8/2018 | Cestero et al. | |

FOREIGN PATENT DOCUMENTS

| | | | |
|---|---|---|---|
| EP | 1949860 | 7/2008 | |
| EP | 2462883 | 12/2011 | |
| EP | 2417922 | 2/2012 | |
| EP | 2524662 | 11/2012 | |
| EP | 2601898 | 6/2013 | |
| WO | WO 90/01298 | 2/1990 | |
| WO | WO 01/80725 | 11/2001 | |
| WO | WO2017027640 | 2/2017 | |
| WO | WO-2017027640 A1 * | 2/2017 | A61B 17/0206 |

* cited by examiner

ADJUSTABLE LOCKING SURGICAL RETRACTOR

PRIORITY PARAGRAPH

This application claims priority to U.S. Provisional Patent Application 62/732,340 filed Sep. 17, 2018, which is incorporated herein by reference in its entirety.

BACKGROUND

Abdominal operations in both emergency and elective surgery settings require adequate exposure of abdominal contents in order for the surgeon to properly visualize areas of injury or disease. This is typically accomplished by the use of static metal retractors. Two of the most common retractor mechanisms in current use are the Balfour retractor and the Bookwalter retractor. Each of these retractors presents advantages and disadvantages in their design and use. The Balfour retractor consists of a frame with integrated metal blades on a ratchet system which, when engaged, retracts the abdominal wall laterally, thereby exposing the abdominal contents and allowing the surgeon to operate. The Bookwalter mechanism consists of a supporting frame attached to the operating table upon which a rigid non-adjustable metal ring is attached to which retractor blades are then attached individually. Despite the ubiquitous use of these retractors, these surgical retractor mechanisms have not been improved upon for considerable time.

The Balfour retractor is perhaps the most commonly utilized abdominal retractor due its simple design, ease of use, and rapid exposure of the abdomen, particularly in trauma and emergency surgery settings when time is of the essence. Since it does not require the attachment of a metal frame to the operating room bed, as with the Bookwalter retractor, valuable time is not wasted and it can be quickly inserted after the abdominal incision is created.

Despite the Balfour retractor's prevalence in operating rooms, and ease of utilization, there are several limitations to its use. It provides inadequate abdominal exposure of large or obese patients. In larger or obese patients, the current design of the standard Balfour retractor often does not provide enough retraction to adequately expose the abdomen. The frame along which the retractor blades run is typically too short for larger or obese patients, resulting in suboptimal exposure and frequently necessitating conversion to another retractor system. Due to the Balfour retractor's inherently limited design, the surgical incision is only retracted along one axis (transverse), limiting overall exposure of the wound. An optional additional retractor blade (bladder blade) can be attached which only adds retraction in the inferior direction, typically resulting in suboptimal exposure requiring conversion to another retractor system.

The standard Balfour retractor does not provide an additional frame upon which to attach additional retractor blades except for a single bladder blade. This significantly limits the ability to retract additional incisional or abdominal contents compared to other retractor mechanisms, thereby limiting surgical exposure. Additionally, the Balfour retractor system commonly poses a significant problem during its use due to the unintentional movement and migration of the retractor blades along the edges of the surgical wound. The two retractor blades which provide lateral traction on the wound edges (or abdominal wall in abdominal operations) frequently unintentionally migrate to either the superior or inferior parts of the wound, causing rotation of the entire retractor mechanism, loss of wound edge retraction, and requiring either time-consuming repositioning of the retractor or conversion to another type of retractor system. This is particularly common in large or obese patients.

Bookwalter retractor is typically the retractor system used when the Balfour retractor system is considered inadequate or ineffective. It consists of a supporting metal rod which is attached to a side rail on the operating room table by a non-sterile individual in the operating room after the patient is under anesthesia (the rail on the operating table is not considered part of the sterile operating field). A second metal arm is then attached to this supporting rod, and a rigid circular or oblong metal ring is then attached to the second metal arm. Once this is in place, individual retractor blades can then be attached, using the rigid ring for support.

Despite the popularity of the Bookwalter retractor it also presents several limitations. The Bookwalter retractor mechanism involves fixation to the operating room table which requires attachment by a non-sterile individual in the operating room. Occasionally this causes concerns in maintenance of the sterile field, as the surgeon may need to place his hands below the sterile barrier in order to assist and properly place the retractor arm. In addition, the multiple arms which require setup before surgical retraction is achieved mandates a significant amount of time in instrument setup, rendering this system inadequate for emergency settings or operations when time is of the essence. The circumferential ring used in the Bookwalter system is not expandable and frequently limits the placement of additional retractors in both the longitudinal and transverse axes. In addition, the fixed sizes of the rings do not allow adjustment of retraction depending on the individual physical characteristics of each patient and various types and sizes of wounds or incisions. The Bookwalter system also requires frequent repositioning by the surgical team during its use. After the Bookwalter system is set up and attached to the bed frame, the ring system is thereby fixed in place and additional retractors are attached. However, as the operation progresses and surgical exposure requirements change, the system, needs to be repositioned to place the static non-expandable ring into the correct location. This requires interruption of the operation, removal of the retractor blades, repositioning of the ring, and reattachment of the retractor blades, again requiring significant time. There is an existing need for additional retractor systems.

SUMMARY

The current disclosure describes an adjustable retractor system that addresses many of the problems outlined above for current retractor systems, while minimizing the number of components. Certain embodiments are directed to a surgical retractor with a frame having an adjustable circumference or width comprising two interconnecting frame segments. In certain aspects the frame has fixed length along one axis and an adjustable length along the other perpendicular axis. In certain aspects the outer edge of the frame segments have a series of ridges forming teeth or grooves along at least a portion of the length, and in certain aspects along the entire length of the outer edge. The frame segment can have a stop mechanism positioned at one or both ends of the frame segment. In certain aspects, the stop, can be anywhere along the length of the frame segment. The stop can be in the form of, a screw, pin, hole, or elevated material that can contact or engage a connector to stop the movement of the frame segment through the connector which can result in disassembly or instability of the retractor. In certain aspects the stop is a screw that can engage threads formed in the frame segment. In certain respects a surgical retractor comprises (a) a retractor frame having an adjustable circumference or width comprising (i) two frame segments, each frame segment comprising a first and second substantially straight and substantially parallel arm portion connected by a middle portion that is substantially perpendicular the arm portions. The frame segments forms two curve portions that connect the arm portions to the middle portion. Each frame segment having a top and bottom face with an inner edge and an outer edge, wherein the frame segments are configured to overlap with a first substantially straight arm portion of one frame segment overlapping a first substantially straight arm portion of the other frame segment, and (ii) connectors configured to receive arm portions of a first and/or second frame segment to form the retractor frame. The connector can be in (i) an unlocked configuration that allows the arm portions of the frame segments to move with respect to one another allowing the circumference of the frame to adjust or (ii) a locked configuration that fixes a first substantially straight arm portion of a first frame segment at a position relative to a first substantially straight arm portion of the second frame segment. In certain aspects, the connector can be affixed or removeably affixed to a frame segment. In a further aspect, a first and second connector can be affixed or removeably affixed to the same frame segment or different frame segments. In certain aspects, the connector(s) are affixed or removeably affixed to the end of a straight arm portion of a frame segment. In certain aspects, the arm portion of one frame segment is not the same as the arm portion of a second frame segment. In other aspects, the arm portions are of equal or similar length. The adjustable retractor can comprise 2, 3, 4, 5, 6 or more retractor blades coupled to the frame segments where the face of the retractor blade forms an angle with, e.g., is substantially perpendicular to, the plane of the frame. In certain aspects the connectors are designed to provide a ratchet mechanism. The ratchet mechanism of the connector is configured to interact with teeth or grooves that are positioned along all or a portion of the inner or outer edge of the frame segments. The connector can include 1, 2, 3, or more a pawls configured to engage one or more frame segment. In certain aspects, the connector comprises individual pawls configured to interact separately and/or independently with individual frame segments. In a further embodiment the connectors can be configured to provide a space between the frame segments faces. If there is space between the frame segments, this space can provide for the insertion of a portion of an attachment (e.g., a lip or protrusion on the attachment) to further stabilize additional attachments that may be affixed to the retractor. The ratchet mechanism allows the frame to be expanded when the connectors are in the locked position but does not allow the contraction of the frame unless a release is engaged. In certain aspects the ratchet mechanism associated with the connectors is a directional ratchet that allows a frame segment to move in one direction that results in expansion of the frame and resists or does not allow movement of the frame segment in the opposite direction, i.e., frame contraction. In a further aspect the edges of the ratchet teeth or groove are beveled to allow for clearance of the ratchet. The connector(s) can further comprise one or more spring loaded brake mechanisms. In certain aspects the retractor can be configured to be stabilized, coupled, or fixed to a subject's body, a wound, an incision, or a cavity. The retractor can be stabilized, coupled, or fixed by a clamp, suture, staple, or other mechanism. In certain aspects the retractor can have an adaptor or be fixed to an adaptor that in turn can be fixed to a support, such as a bed or operating table.

In another embodiment a retractor blade is attached to a retractor blade connector. The retractor blade connector can be configured to allow the adjustment of the retractor blades up and down with respect to the frame segments or to be moved and secured along the frame segments. The retractor blade connector can form a passage through which the proximal portion of the retractor blade can pass through. The passage being configured with a retractor blade locking mechanism that reversibly fixes the retractor blade at a particular position or depth. The locking mechanism can be a pin, a screw, or other locking mechanism that can reversibly engage the proximal portion of the retractor blade to hold it in place when engaged and allow its movement when disengaged. In certain aspects the locking mechanism can include a spring to assist in engaging the mechanism and resisting the disengagement of the mechanism. In certain aspects the pin or screw can pass through an opening in the retractor blade connector body or be attached to the top or bottom of the retractor blade connector body. The proximal portion of the retractor blade can have an adjustment portion that passes through the retractor blade connector. The adjustment portion can have grooves, holes, or teeth to engage the retractor blade locking mechanism. The connector can further comprise a removable stop coupled with a prescribed slot or pattern of holes formed in the frame segment that together are configured to reversibly lock the connector in place. In certain aspects, the connectors are configured to allow one or more frame segments to be expanded and do not allow one or more frame segments to be contracted. The connectors can be configured to be affixed to at least one frame segment. The frame segments may be unequal in length. In certain aspects, the frame segments are equal in length.

In certain aspects the retractor frame when assembled is a rounded polygon, e.g., a quadrilateral (square or rectangle). In a further aspect the frame is a rounded quadrilateral. In still a further aspect the frame is a rounded rectangle. The frame can be comprised of two frame segments. A frame segment includes two substantially straight arm portion on each end and a middle portion connecting the substantially straight arm portions forming a U shaped frame segment.

In certain aspects the outer edge, inner edge, or outer edge and inner edge of the frame segment is toothed and/or grooved along at least a portion of the segment. In a further aspect the top face, bottom face, or top and bottom face comprise a series of grooves or ridges as well.

In certain aspects the top, bottom, or top and bottom faces are substantially planar. In a further aspect the top, bottom, or top and bottom faces are curved (concave or convex) along the short axis of the segment.

In certain aspects each of the frame segments (substantially straight arms and middle portion) are independently about 2.5, 5, 10, 15, 20, 25, 30, 35, 40, 45, to 50 centimeters in length as measured along the non-curved or substantially straight portion, and can include all values and ranges there between. In a further aspect a first substantially straight arm portion of a segment is about 2.5 to 50, 5 to 40, 5 to 30, 5 to 20, 5 to 100, 10 to 40 or 10 to 30 centimeters in length as measured along the non-curved or substantially straight portion and a second substantially straight arm portion is about 2.5 to 50, 5 to 40, 5 to 30, 5 to 20, 5 to 100, 10 to 40 or 10 to 30 centimeters in length as measured along the non-curved or substantially straight portion. The arms of a frame segment need not, but may be the same length, where different length arms will be complemented by the other frame segment in the frame. In a further aspect a middle portion of a frame segment is about 2.5 to 50, 5 to 40, 5 to 30, 5 to 20, 5 to 100, 10 to 40 or 10 to 30 centimeters in length as measured along the non-curved or substantially straight portion. In certain aspects the first and second arm portions are of equal length. The length of arm portion is measured from the end of the segment to beginning of the curve portion of the segment (along the non-curved or substantially straight portion). In certain aspects the rounded angle of the frame segment is approximately 90 degrees (+/−0.5, 1, 2, to 5 degrees). In a further aspect the arm portions of individual frame segments are positioned having the inner edge of first arm portion aligned substantially parallel to the outer end of a second frame segment. In another aspect the top face of a first frame segment can face the bottom face of a second frame segment. The frame segment faces can be in contact with each other or form a gap or space between the frame segments when assembled. In certain embodiments the retractor, in an expanded configuration, has an adjustable internal distance of 2.5, 5, 10, 15, 20, 25, 30, 35, 40, 45, 50, 55, 60, 65, 70, 75, 80, 85, to 90 centimeters, including all ranges and values there between.

In certain aspects 2, 3, 4, 5, 6 or more retractor blades are coupled to the retractor frame. The retractor blade can have a distal blade portion and a proximal connector or adjustment portion. In a further aspect at least 2 retractor blades are coupled to the frame. In other aspects at least 4 retractor blades are coupled to the frame. In particular aspects 6 retractor blades are coupled to the frame. In a further aspect at least one retractor blade is coupled to a retractor blade connector. In certain aspects at least one retractor blade is coupled to a frame segment. In a further aspect at least one retractor blade is configured to be moveable along the retractor frame. In still a further aspect the retractor blade is configured to be moveable up and down with respect to the retractor frame.

Certain embodiments are directed to a surgical retractor frame segment which comprises a first and second substantially straight arm portion connected by a substantially straight middle portion; the frame segment having a curve portion between the arm portions and the middle portion, where the long axis of the middle portion is approximately perpendicular to the long axis of the arm portions, the arm portion projecting to the same side from the middle portion. In certain aspects the arm portions are substantially parallel to each other. Frame segments have a top and bottom face with an inner edge and an outer edge. The frame segment can further comprise one or more expansion stops that can be reversibly connected to the frame segment and form a protrusion on the top or bottom face of the frame segment, the stop can be positioned at or near one or both ends and/or both faces of the frame segment.

Other embodiments are directed to a surgical retractor connector comprising a body forming two or more lumens, each lumen configured to receive arm portions of separate frame segments. In certain embodiments the surgical retractor connector can include a ratchet mechanism configured to interact with at least one edge (i.e., the inner, outer, or inner and outer edge(s)) of the frame segment when inserted into the surgical retractor connector lumen. The surgical retractor connector can be in (i) an unlocked configuration that allows the arm portions of the frame segments to move with respect to one another allowing the retractor frame to adjust or (ii) a locked configuration that fixes an arm portion of a first frame segment at a position relative to a first arm portion of a second frame segment. The connector can further comprise or be configured to include a retractor blade positioned below the frame and can form a prescribed angle (e.g., perpendicular to) the plane of the frame. The retractor blade can be fixed to the connector body or removeably connected to the connector body by a retractor blade connector.

Certain embodiments are directed to methods of using the surgical retractor described herein, the method comprising: inserting retractor blades of a contracted retractor in a wound or incision, expanding the surgical retractor to expose a body cavity, and locking the retractor in position.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Attachment of the surgical retractor described herein to an operating table or other support is not necessary, but can be an option, and therefore use of the surgical retractor described herein does not require involvement of any non-sterile member of the operating team. In addition, the lack of an obtrusive fixed metal frame allows the surgeon increased mobility and positioning at the sides of the patient during the operation. The system remains sterile, and its simple and rapid deployment can be applied to emergency and time sensitive situations.

The adjustable/expandable system comprising frame segments expanded on connectors or locking ratchet mechanisms allows full exposure of the surgical wound, as the ratchet mechanisms attached to the frame segments allow the wound to be maximally retracted. This design allows the incision to be retracted to its maximal possible dimensions, as it is not limited by the use of a pre-determined ring size (as in the Bookwalter retractor).

The expandable locking surgical retractor allows the subsequent attachment of multiple retractor blades to provide additional surgical exposure (similar to the Bookwalter retractor). The frame also allows the use of lighting options which attach directly to the frame, improving surgical visualization and illumination of deep wounds and/or spaces.

Figure 8:
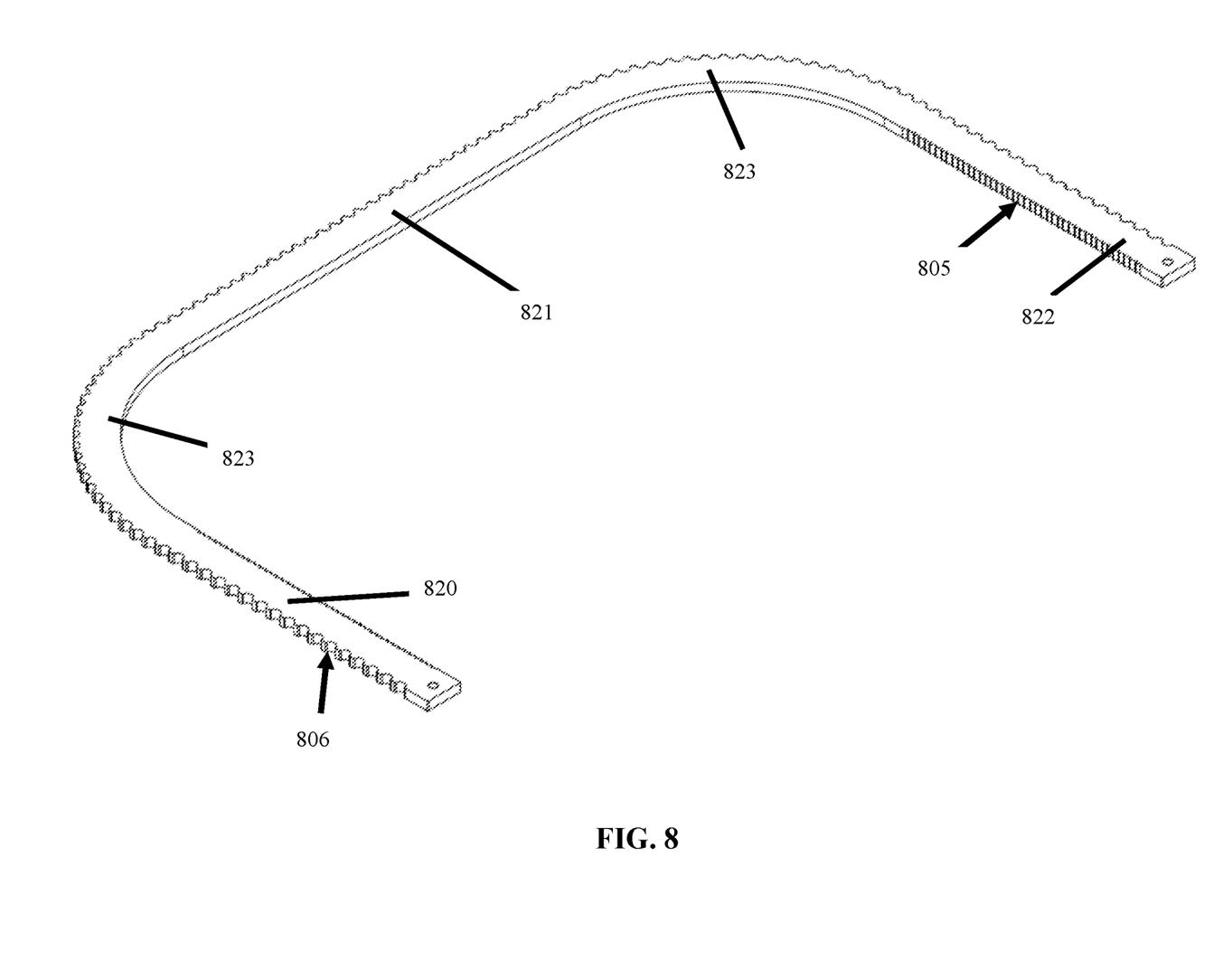
FIG. 8 is a perspective illustration of one embodiment of a frame segment in isolation.
Figure 9:
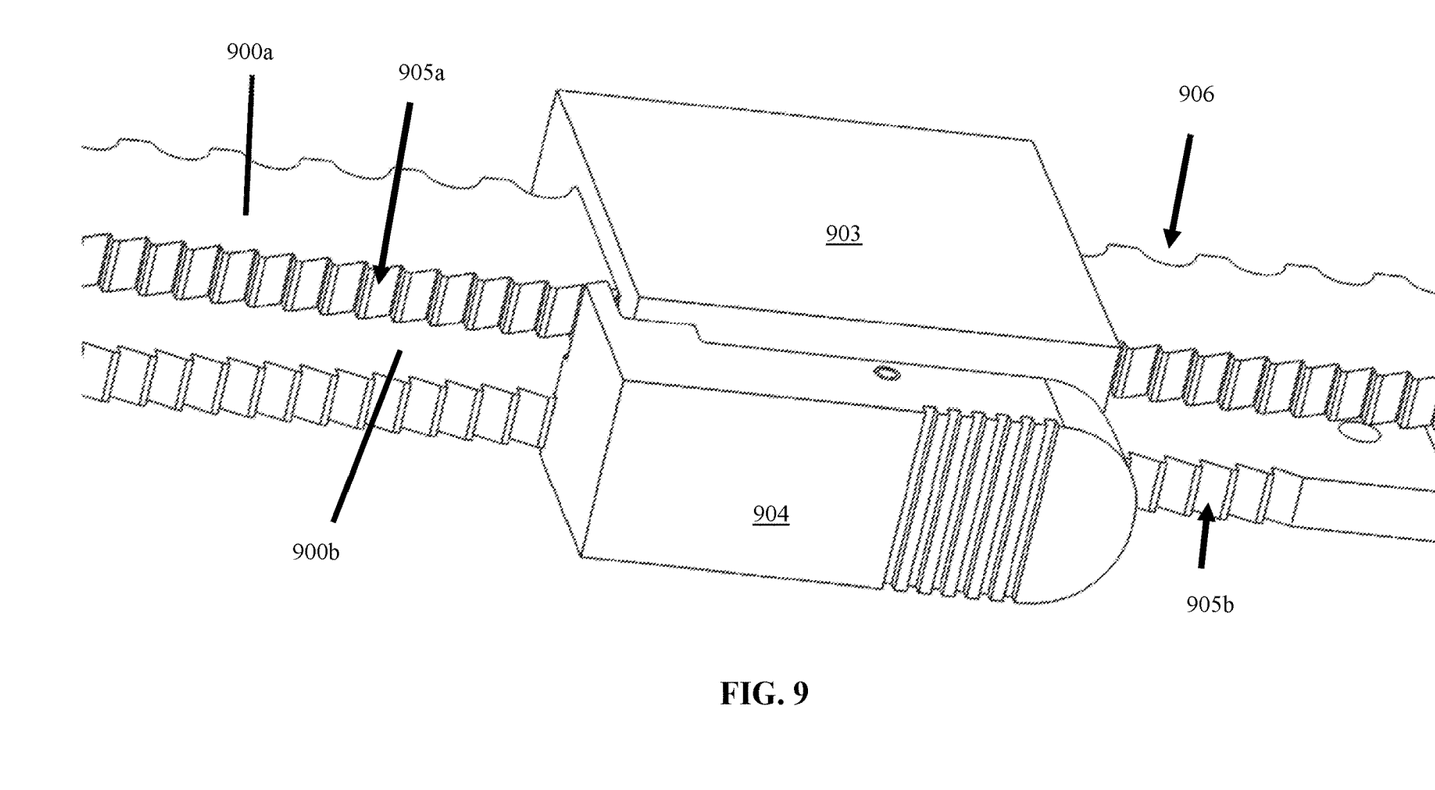
FIG. 9 is a focused perspective illustration of one embodiment of a surgical retractor connector in a surgical retractor assembly in a fully expanded configuration.

The surgical retractor described herein can comprise two frame segments forming a retractor frame by connecting the frame segments with a connector or retractor frame connector (see FIG. 9). In certain aspects the retractor comprises two frame segments joined by two connectors. In certain embodiments a segment will have two substantially straight arm portions joined by a middle portion having a curved portion connecting each substantially straight arm portion, forming a U-shaped frame segment (see FIG. 8). The segments are configured to be assembled to form a rounded polygon, rounded rectangular, frame. Each segment comprises a top and bottom surface/face with an inner edge facing the inside of the assembled frame and an outer facing outward.

Figure 1:
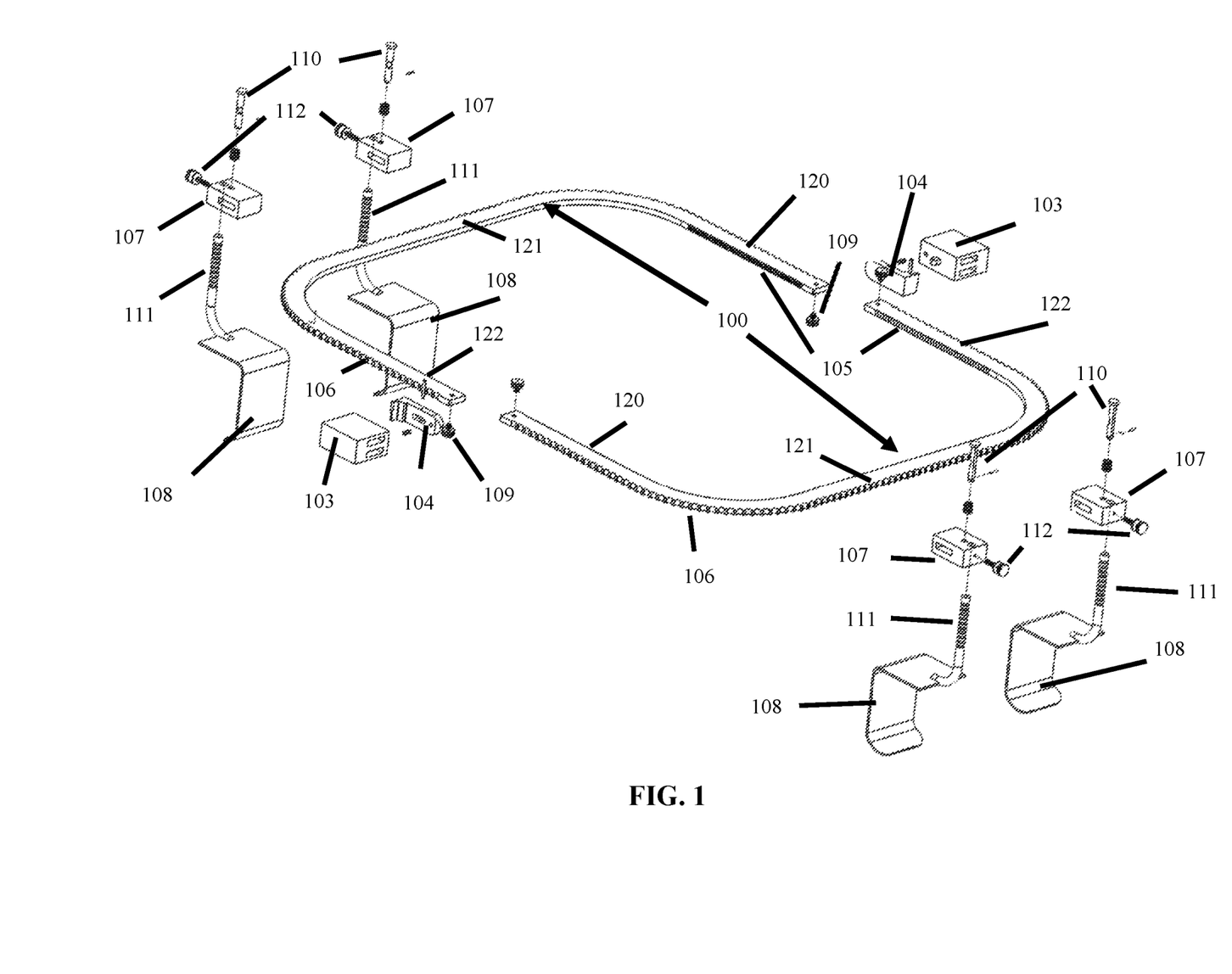
FIG. 1 is an illustration of air exploded view of one embodiment of an adjustable retractor assembly.

FIG. 1 shows one embodiment of a surgical retractor frame in an exploded view. In certain embodiments the frame comprises two frame segments 100. Each frame segment 100 has two arm portions 120 and 122 connected by a middle portion 121. Frame segments are connected using connector 103. The frame segments can have teeth or grooves 105 along one or more edges, and/or ridges or grooves (105 or 106) along one or more face. In certain aspects the inner edge of frame segment 100 is configured to interact with connector 103, connector 103 can have ratchet mechanism 104 and portions of the frame segment 100 can have ratchet teeth 105 and/or 106 along an edge and/or a face of the frame segment. The inner edge faces the interior of the opening formed by assembly of frame segments 100. In other aspects frame segments 100 can have notches, grooves, or teeth 105 and/or 106 that can be utilized for securing attachments and the like. In certain aspects notches, grooves, or teeth 106 can be positioned in the outer edge of segment 100, the upper face of segment 100, the lower face of segment 100, or combinations thereof. Arm portions (also referred to as substantially straight arm portions herein) 120 and 122 of separate frame segments can be connected by connector 103. In certain embodiments connector 103 comprises a ratchet mechanism 104 that interacts with ratchet teeth 105 to adjustably secure arm portions 120 and 122 and allowing expansion and contraction of the assembled frame as well as stabilizing the frame once a desired configuration is achieved. In certain aspects a retractor blade connector 107 can have a fixed or removable retractor blade 108. In certain aspects the frame segment 100 has an expansion stop 109 that protrudes from the face of the frame segment and stops the expansion of the arm portions through the connector. The expansion stop can be a screw, a clip, a pin, or other mechanism that is configured to not allow the frame segment to pass through connector 103.

With further reference to FIG. 1, the retractor blades 108 can be configured to move up and down with respect to the frame. In this embodiment retractor blade connector 107 can be configured to provide for movement of retractor blade. Retractor blade connector 107 can be fixed to the frame using a retractor blade connector locking mechanism 110. The mechanism can include a screw, pin, spring loaded pin or similar adjustable locking mechanisms. Retractor blade connector 107 can be configured to receive the proximal portion (111) of a retractor blade. The proximal portion of the retractor blade can be reversibly locked by using a retractor blade locking mechanism 112. The proximal portion of the retractor can form a retractor blade locking mechanism receiver. The locking mechanism receiver can be a notch, a hole, a cavity or other structure to receive the locking mechanism. When the locking mechanism is engaged the retractor blade is reversibly fixed at that particular position. If one wanted to adjust the retractor blade one would disengage locking mechanism, move the retractor blade to a new position, and fix that position by engaging locking mechanism with the locking mechanism receiver.

Figure 2:
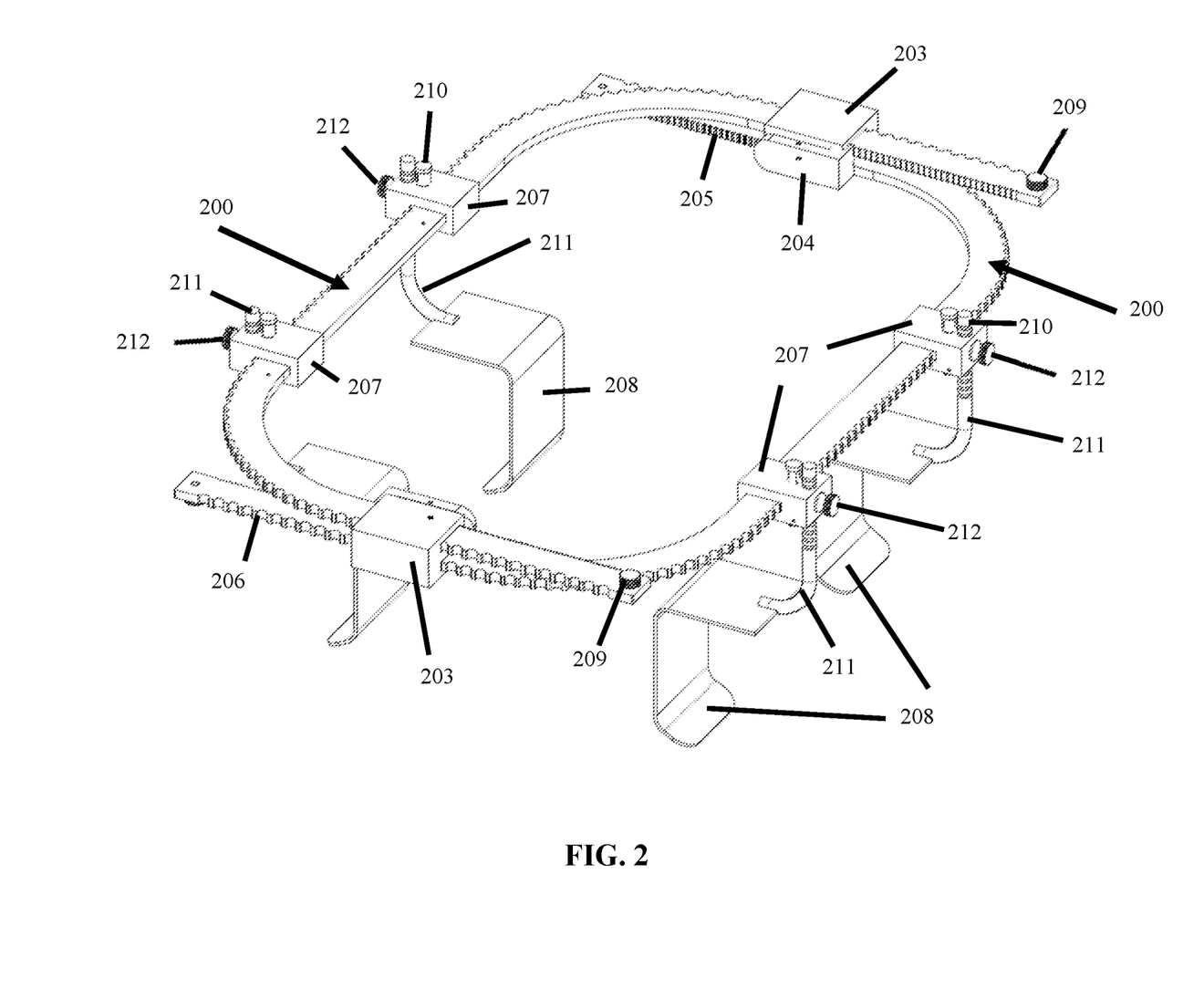
FIG. 2 is a perspective illustration of one embodiment of an adjustable retractor assembly.

FIG. 2 shows one embodiment of an assembled retractor frame. Connectors 203 are configured with a release/locking mechanism that allows a person to release frame segment 200 and allow expansion or contraction of the frame as well as providing a locking mechanism to secure the segments in place when desired. In certain aspects connectors 203 comprise a locking, ratchet mechanism 204. In another embodiment the frame segment has a stop mechanism 209 that will stop the expansion of the frame at a selected point. The expansion stop is an elevated portion that cannot pass through the connector resulting the stopping of the frame expansion at the point to the expansion stop. The expansion stop can be a screw or a pin that can be engaged or disengaged as needed. Typically, the expansion stop would be engaged during use to prevent over extension. In certain embodiments not only does the frame have a mechanism for adjustment, but so does the retractor blade portion 208 of the device (212). Retractor blade 208 can have a portion that is proximal to the frame (proximal portion 211) that passes through retractor blade connector 207 and can engage a retractor blade locking mechanism 210 to be reversibly fixed in position. Reversibly fixed means that it will maintain its position until a locking mechanism is disengaged or the engagement is reversed allowing freedom of movement when disengaged. In certain aspects the proximal portion can have one or more locking mechanism receivers that receive the locking mechanism. Also shown in FIG. 2 are notches, grooves, or teeth (ratchet teeth 205 and/or grooves 206) that can be utilized for securing attachments or connectors and the like to the frame.

Figure 3:
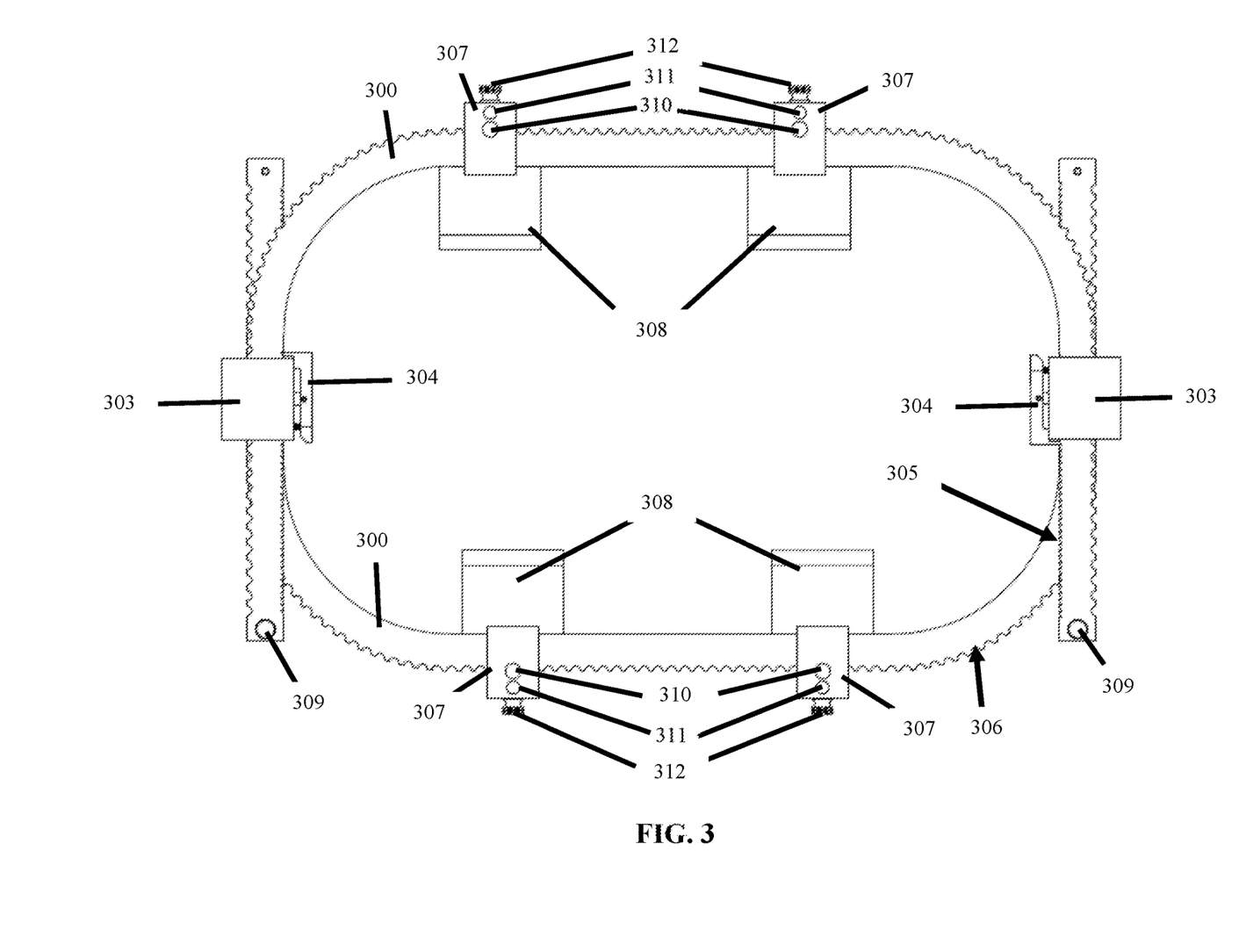
FIG. 3 is a top view illustration of one embodiment of an adjustable retractor assembly.

FIG. 3 is a top down view of the assembled frame showing frame segment connectors 303 connecting frame segments 300 with example of a frame locking mechanism 309 to secure the segments in place when desired. In certain aspects connectors 303 comprise a locking, ratchet mechanism 304. Also illustrated are frame segment stop mechanism 309. Retractor blade portions 308 are shown with proximal portion 311 of the retractor blade is shown traversing retractor blade connector 307. Retractor blade 308 can be reversibly positioned on the frame using retractor blade locking mechanism 312 The retractor connector locking mechanism 312 is shown interacting with a locking pin 310 that fits in a groove 306. Also shown in FIG. 3 are notches, grooves, or teeth (ratchet teeth 305 and/or grooves 306) that can be utilized for securing attachments or connectors and the like to the frame.

Figure 4:
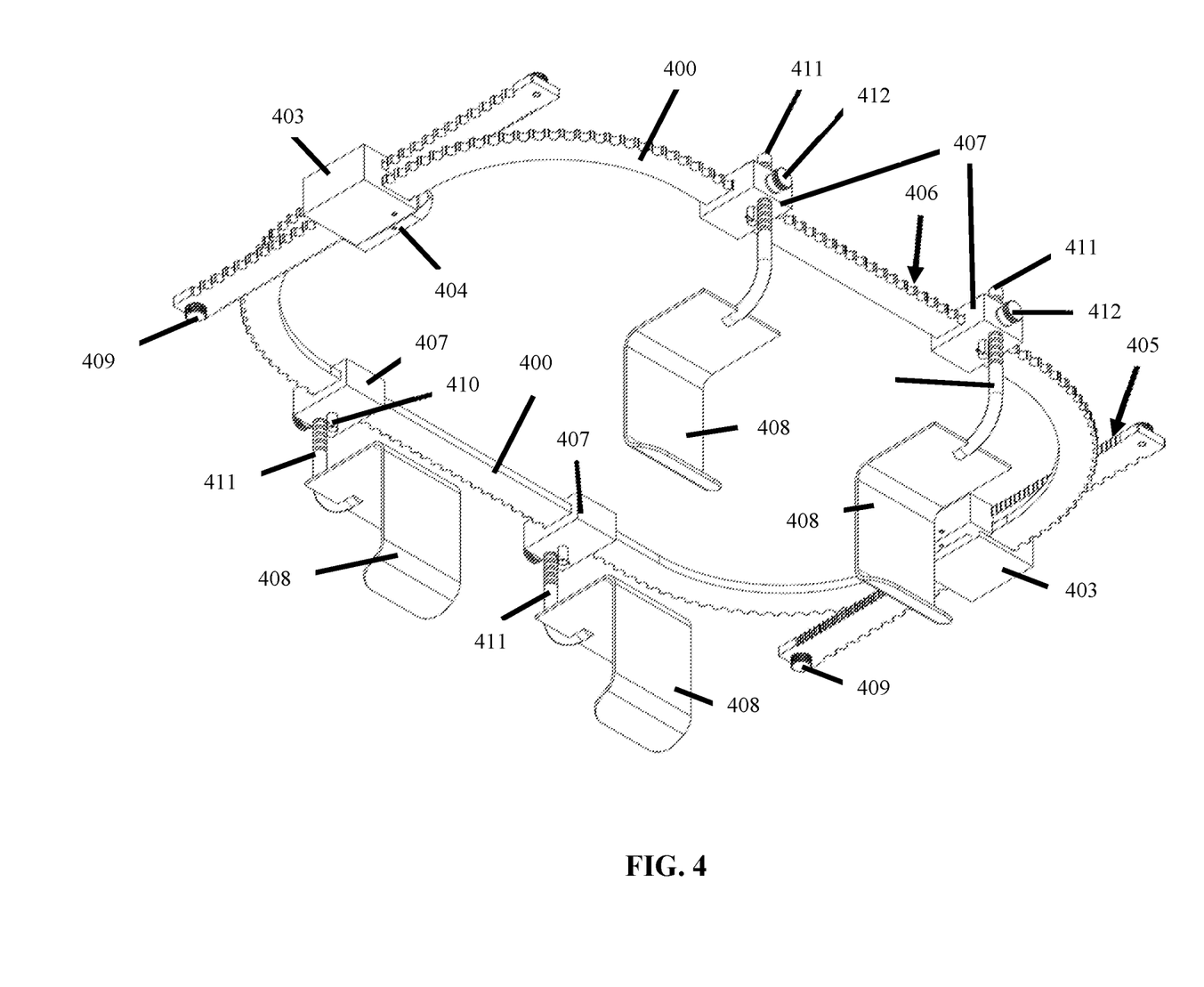
FIG. 4 is a bottom-up perspective illustration of one embodiment of an adjustable retractor assembly.

FIG. 4 is a bottom up perspective view of the assembled frame showing frame segment connectors 403 connecting frame segments 400 with example of a frame locking mechanism 409 to secure the segments in place when desired. In certain aspects connectors 403 comprise a locking, ratchet mechanism 404. Also illustrated are frame segment stop mechanism 409. Retractor blade portions 408 are shown with proximal portion 411 of the retractor blade is shown traversing retractor blade connector 407. Retractor blade 408 can be reversibly positioned on the frame using retractor blade locking mechanism 412 The retractor connector locking mechanism 412 is shown interacting with a locking pin 410 that fits in a groove 406. Also shown in FIG. 4 are notches, grooves, or teeth (ratchet teeth 405 and/or grooves 406) that can be utilized for securing attachments or connectors and the like to the frame.

Figure 5:
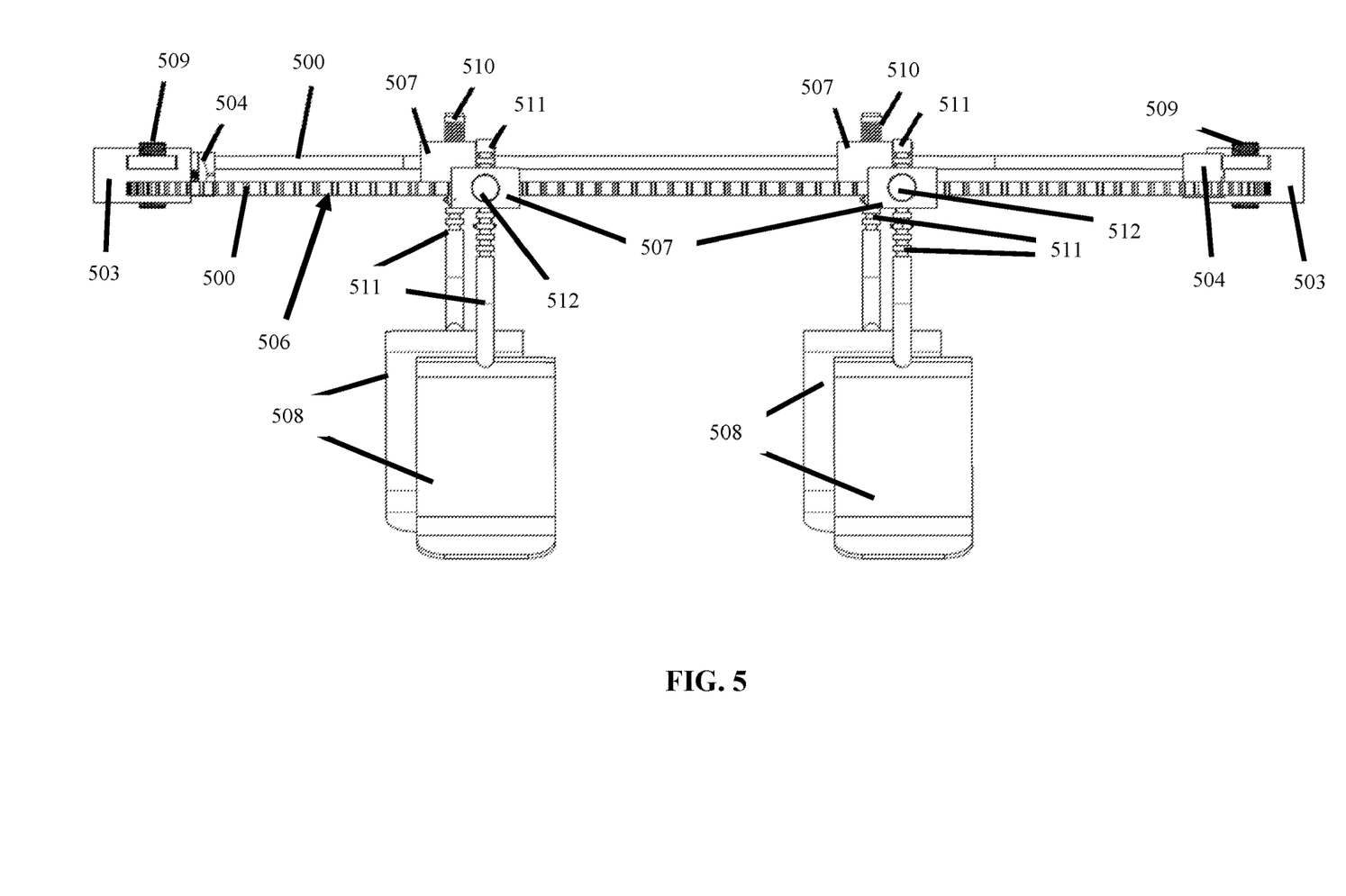
FIG. 5 is a side view illustration of one embodiment of an adjustable retractor assembly.

FIG. 5 is a side view of the assembled frame showing frame segment connectors 503 connecting frame segments 500 with example of a frame locking mechanism 504 to secure the segments in place when desired. In certain aspects connectors 503 comprise a locking, ratchet mechanism 504. Also illustrated are frame segment stop mechanism 509. Retractor blade portions 508 are shown with proximal portion 511 of the retractor blade is shown traversing retractor blade connector 507. Retractor blade 508 can be reversibly positioned on the frame using retractor blade locking mechanism 512 The retractor connector locking mechanism 512 is shown interacting with a locking pin 510 that fits in a groove 506. Also shown in FIG. 5 are notches, grooves, or teeth (grooves 506) that can be utilized for securing attachments or connectors and the like to the frame.

Figure 6:
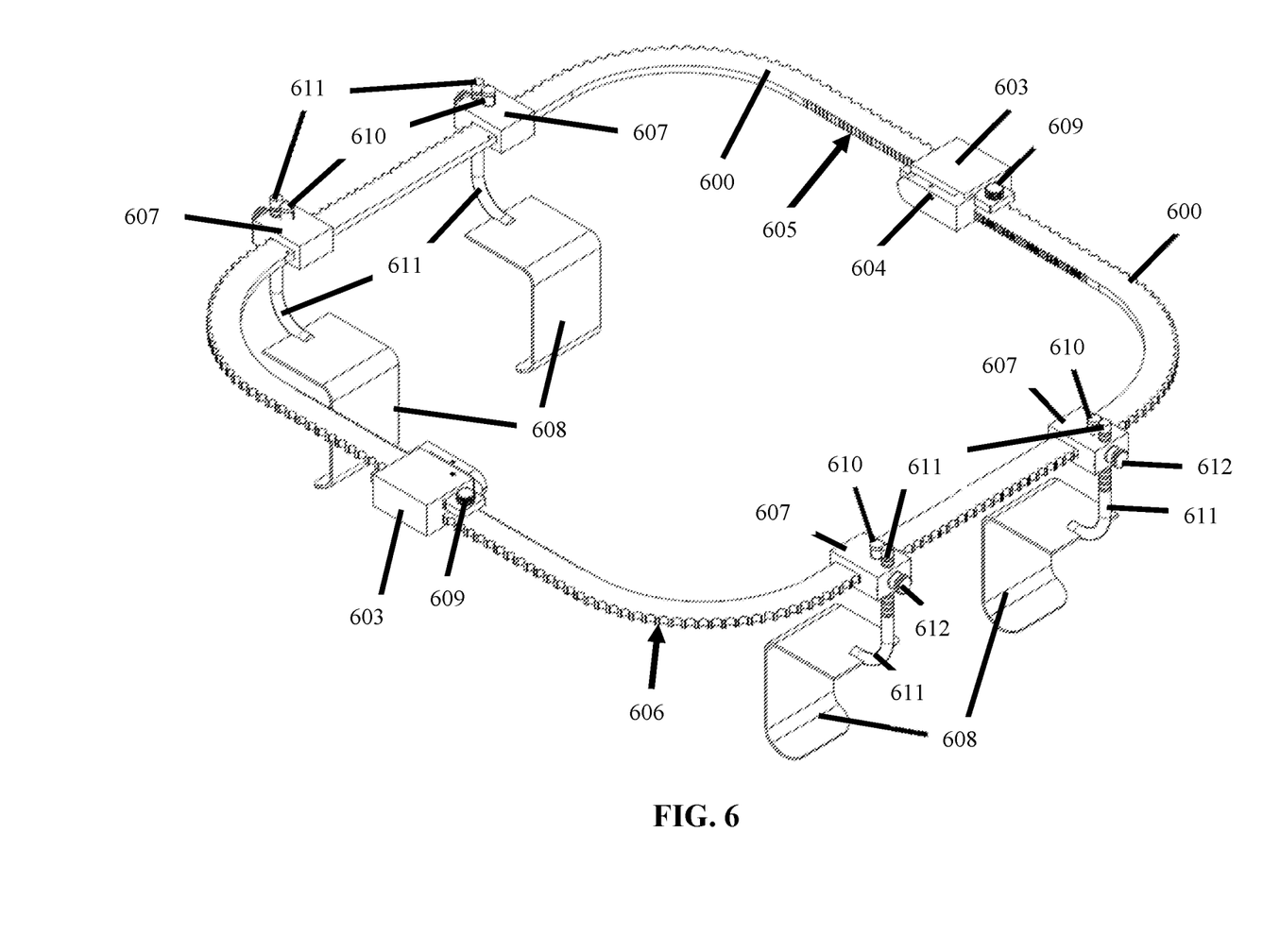
FIG. 6 is a perspective illustration of one embodiment of an adjustable retractor assembly in a fully expanded configuration.

FIG. 6 is a top perspective view of the assembled fully extended frame showing frame segment connectors 603 connecting frame segments 600 with example of a frame locking mechanism 604 to secure the segments in place when desired. In certain aspects connectors 603 comprise a locking, ratchet mechanism 604. Also illustrated are frame segment stop mechanism 609. Retractor blade portions 608 are shown with proximal portion 611 of the retractor blade is shown traversing retractor blade connector 607. Retractor blade 608 can be reversibly positioned on the frame using retractor blade locking mechanism 612 The retractor connector locking mechanism 612 is shown interacting with a locking pin 610 that fits in a groove 606. Also shown in FIG. 6 are notches, grooves, or teeth (ratchet notches 605 and grooves 606) that can be utilized for securing attachments or connectors and the like to the frame.

Figure 7:
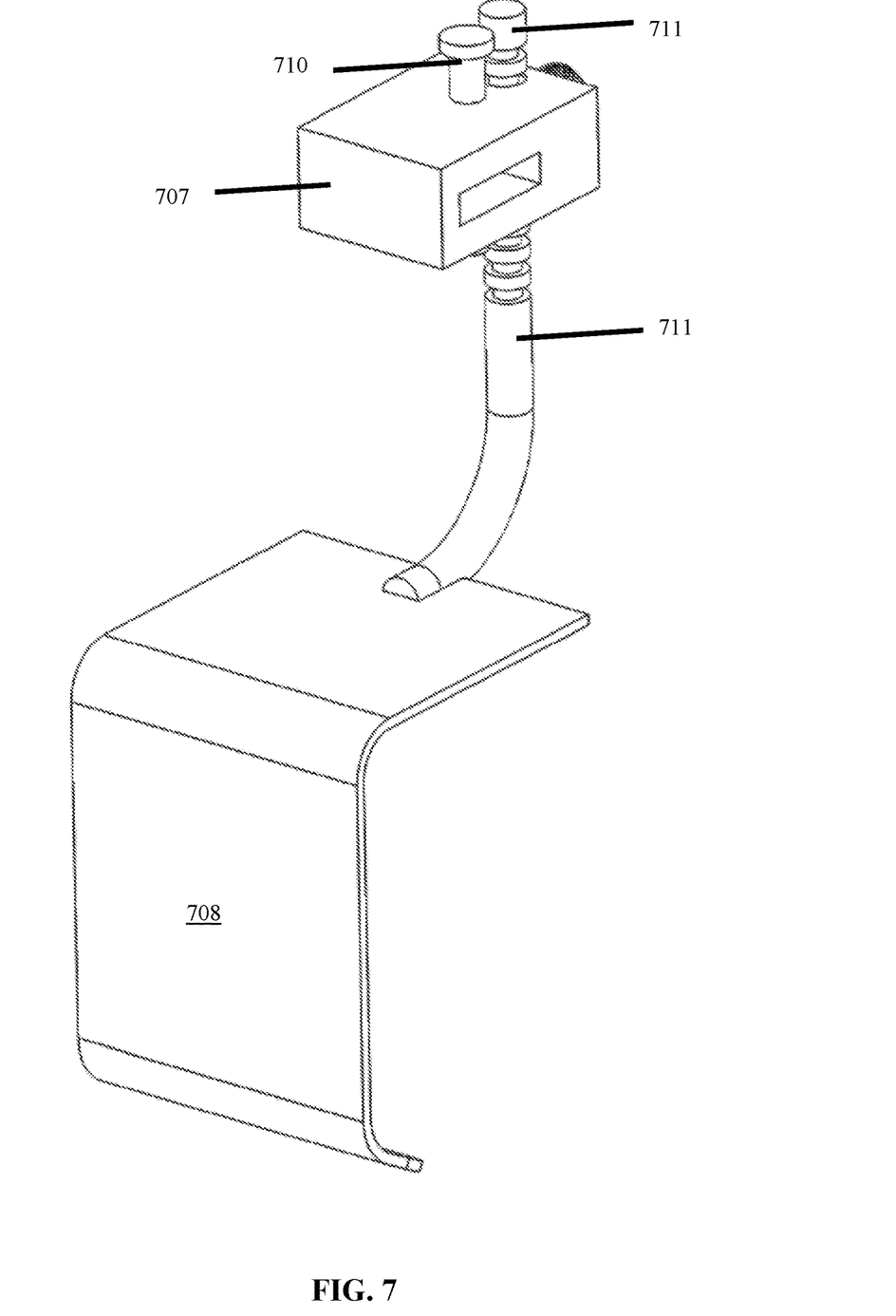
FIG. 7 is a perspective illustration of one embodiment of a retractor blade assembly in isolation.

FIG. 7 shows a retractor blade assembly in isolation. Retractor blade 708 are shown with proximal portion 711 of the retractor blade is shown traversing retractor blade connector 707. Retractor blade 708 can be reversibly positioned on the frame using retractor blade locking mechanism. The retractor connector locking pin 710 fits in a groove or other frame element.

FIG. 8 shows a frame segment in isolation. A frame segment has a first arm (substantially straight arm) portion 820 and a second arm (substantially straight arm) portion 822 connected by a middle portion 821. Each arm portion 820/822 of a frame segment is configured to interact with a connector in a way that allows assembly and adjustment of the assembled frame of the retractor. The inner edge of the arm portion can be configured to allow connector release/locking (e.g., ratchet 805). In certain aspects the outer edge can be configured to interact with the connector, alone or in combination with the inner edge, e.g., grooves 806. The middle portion 821 is the portion of the frame segment between the arm (substantially straight arm) portions 820. The middle portion 821 having curved portions 823 that connects the arm (substantially straight arm) portions 820/822 to the middle portion 821. In certain aspects, when there are two opposing U-shaped frame segments positioned to be moved apart to open an abdomen, for example, and the retractor configured to lock in place to prevent collapse as it is being expanded and a connector configured with one pawl for release of both frame segments then in this configuration the teeth on the frame segment for interacting with the pawl can be cut or configured in opposite directions to provide locking during expansion using a single pawl. In other aspects an individual pawl can be provided in the appropriate configuration so that the teeth need not be cut or positioned in opposite directions. Teeth on individual frame segments can be cut or configured in the same or counter directions so when the retractor is assembled the teeth are all pointing in opposite directions or in the same direction, respectively.

FIG. 9 shows one embodiment of frame segment connector (or connector) 903 and frame segment 900 assembly in isolation. Each connector 903 can have one or two receiving openings for receiving the arm portions of two frame segments (900a and 900b). In certain aspects opening can be offset, stacked, or side-by-side. In certain aspects the openings are offset. In other aspects the openings are stacked. In certain aspects a connector 903 has one opening (e.g., when a connector is a fixed, integral part of one end of a frame segment); or it can have two or more openings. In certain embodiments one frame segment is attached to two connectors, for example, the connector can be fixed to one or both ends of a frame segment. In other aspects one connector can be adjustably connected to two frame segments, for example the connector has one or two openings for receiving an arm portion of a first frame segment and an arm portion of a second frame segment. The frame segments can be attached, coupled, or connected through a shared connector. Connector 903 can comprise a ratchet(s) or pawl(s) 904, which are configured to ratchet in opposite directions. Ratchet(s) or pawl(s) 904 can be configured to interact with a toothed surface of two adjacent segments (e.g., 905a and 905b). The ratchet(s) or pawl(s) can be configured to allow the frame to be expanded by applying a force away from the centerpoint of the retractor without disengaging the ratchet. In other aspects the ratchet is configured to not allow contraction of the frame unless the ratchet is disengaged. Other release/locking mechanisms can be integrated into the current design, so the ratchet mechanism is just one example. The connector can include 1, 2, 3, or more ratchets or pawls configured to engage one or more frame segment. In certain aspects, the connector comprises individual ratchets or pawls configured to interact separately and/or independently with individual frame segments.

The position of the connector along a segment can be fixed by engaging a lock mechanism that can engage the teeth or grooves of a frame segment(s) for locking purposes. In other embodiments the connector can be integrated into one end of the frame segment, in this case the connector may only have one opening and one ratchet mechanism since the connector is fixed at one end of the segment.

A retractor blade need not be associated with the connector. A retractor blade or other implement can be fixed to one or more retractor blade connector or can be an accessory implement that attaches to the frame at positions other than the connector points. A plurality of retractor blades or other implements can be attached to the frame, in certain aspects 2, 3, 4, 5, 6, 7, 8, 9, 10 or more retractor blades and/or other implements can be attached to the frame. The only limiting factor for attachment is the space available along the frame and physical interference between attachments.

A frame segment comprises various regions or portions. A frame segment has a first arm (substantially straight arm) portion and a second arm (substantially straight arm) portion connected by a middle portion. Each arm portion of a frame segment is configured to interact with a connector in a way that allows assembly and adjustment of the assembled frame of the retractor. The inner edge of the arm portion can be configured to allow connector release/locking. In certain aspects the outer edge can be configured to interact with the connector, alone or in combination with the inner edge. The middle portion is the portion of the frame segment between the arm portions. The middle portion has a curved portion that connects the arm portions to the middle portion. The curve portion forms an angle between the arm portions and the middle portion. The curve portion can be characterized by the angle formed between the long axis of an arm portion and middle portion. In certain aspects this angle is between 85 and 95 degrees. In certain aspects the segment angle is or is about 90 degrees.

The frame segment, connector, and retractor blade can be metallic, metallic alloy, plastic, or combination thereof. In certain aspects the retractor is made of material that can be autoclaved or otherwise sterilized (e.g., irradiated, etc.). The frame segment can be a formed rod (having a bend or angle) with circular, oval, square, or rectangular cross section. The connectors are configured to receive and reversibly engage the frame segments of the frame. The segments are coupled connectors to form a retractor frame. Each connector couples two segments.

The invention claimed is:

1. A surgical retractor comprising:
   an adjustable retractor frame having an adjustable circumference comprising a first frame segment and a second frame segment and two connectors;
   the first frame segment and the second frame segment each comprising a first and a second substantially straight arm portion and a middle portion connecting the first and second substantially straight arm portions, the first and second substantially straight arm portion and the middle portion substantially in the same plane and each segment having a continuous fixed length, the long axes of the first and second substantially straight arm portions being parallel to each other and projecting to the same side of the middle portion, the middle portion forming a first and a second bend with the first and second substantially straight arm portions, respectively so that the long axis of the middle portion is perpendicular to the long axes of the first and second substantially straight arm portions, each frame segment having a top and bottom face with an inner edge and an outer edge;
   the first frame segment and the second frame segment configured to connect to form said adjustable retractor frame when the first substantially straight arm portion of the first frame segment connects with the first substantially straight arm portion of the second frame segment and the second substantially straight arm portion of the first frame segment connects with the second substantially straight arm portion of the second frame segment;
   the connectors configured to receive the first and second substantially straight arm portions of the first and second frame segments to form the adjustable retractor frame, wherein the connector can be in (i) an unlocked configuration that allows the substantially straight arm portions of the frame segments to move with respect to one another allowing the adjustable retractor frame to adjust or (ii) a locked configuration that fixes a substantially straight arm portion at a position relative to a substantially straight arm portion of the other frame segment; and
   two or more retractor blades coupled to the frame where the face of the retractor blade forms an angle with the plane of the frame.

2. The retractor of claim 1, wherein the frame segments further comprise an expansion stop on one or both faces and at one or both ends of the frame segment that is configured to stop expansion of the frame prior to a frame segment passing completely through a connector.

3. The retractor of claim 1, wherein each of the connectors comprise a removable stop coupled with a prescribed slot or pattern of holes formed in the frame segment that together are configured to reversibly lock the connector in place.

4. The retractor of claim 1, wherein the connectors are configured to allow one or more frame segments to be expanded and do not allow one or more frame segments to be contracted.

5. The retractor of claim 4, wherein the connectors are affixed or removeably affixed to at least one frame segment.

6. The retractor of claim 4, wherein each of the connectors comprises a pawl configured to engage one or more frame segment.

7. The retractor of claim 6, wherein the connectors comprise individual pawls configured to interact with individual frame segments.

8. The retractor of claim 1, wherein each of the connectors is configured to position the ends of the frame segments in a stacked configuration.

9. The retractor of claim 1, wherein each of the connectors is configured to position the ends of the frame segments in an offset configuration.

10. The retractor of claim 1, wherein each of the connectors comprises a motorized, controlled, screw drive, worm gear, or removable locking system that allows the movement of both adjacent frame segments towards or away from each other allowing the frame to be contracted or expanded when using the system.

11. The retractor of claim 1, wherein each of the connectors comprises one or more spring loaded brake mechanisms.

12. The retractor of claim 1, further comprising:
two or more retractor blade connectors for coupling the two or more retractor blades to the adjustable retractor frame;
wherein each of the two or more retractor blades are adjustable, each of the two or more retractor blade connectors being configured to receive a proximal portion of one of said two or more retractor blades and to reversibly fix a retractor blade position with a retractor blade locking mechanism incorporated therein, wherein the proximal portion of the retractor blade is moveable up and down until locked by said retractor blade locking mechanism.

13. The retractor of claim 1, wherein the outer edge of each of the first and second frame segment forms one or more notches or teeth.

14. The retractor of claim 13, wherein the teeth of the first frame segment are directed in an opposite direction relative to the teeth of the second frame segment when the first frame segment and the second frame segment are connected to form said adjustable retractor frame.

15. The retractor of claim 1, wherein the substantially straight arm portions of adjacent frame segments are positioned having the inner edge of one substantially straight arm portion aligned substantially parallel to the outer edge of an adjacent frame segment.

16. The retractor of claim 1, wherein the substantially straight arm portions of each of the first and second frame segment are about 2.5 to 50 centimeters in length and the middle portion of each of the first and second frame segment is about 2.5 to 100 centimeters in length.

17. The retractor of claim 1, wherein the adjustable retractor frame in an expanded configuration has an adjustable internal distance of 2.5 to 90 centimeters.

18. The retractor of claim 1, wherein 2, 3, 4, 5, or 6 retractor blades are coupled to the adjustable retractor frame.

* * * * *